United States Patent
Patel et al.

(10) Patent No.: US 11,439,617 B2
(45) Date of Patent: Sep. 13, 2022

(54) POLYMERIC COMPOSITIONS OF MONOMETHYL FUMARATE AND THEIR USE IN TREATING RELAPSING REMITTING MULTIPLE SCLEROSIS AND PSORIASIS

(71) Applicant: DYNAMIC BIOLOGICS INC., Monmouth Junction, NJ (US)

(72) Inventors: Deven Patel, Cedar Grove, NJ (US); H. Rajan Sharma, Belle Mead, NJ (US); Manoj Mishra, Woodstock, MD (US)

(*) Notice: Subject to any disclaimer, the term of this patent is extended or adjusted under 35 U.S.C. 154(b) by 0 days.

(21) Appl. No.: 16/756,842

(22) PCT Filed: Oct. 16, 2018

(86) PCT No.: PCT/US2018/056054
§ 371 (c)(1),
(2) Date: Apr. 16, 2020

(87) PCT Pub. No.: WO2019/079277
PCT Pub. Date: Apr. 25, 2019

(65) Prior Publication Data
US 2020/0237704 A1  Jul. 30, 2020

Related U.S. Application Data

(60) Provisional application No. 62/573,103, filed on Oct. 16, 2017.

(51) Int. Cl.
| | | |
|---|---|---|
| A61K 31/225 | (2006.01) | |
| A61K 9/00 | (2006.01) | |
| A61K 47/60 | (2017.01) | |
| A61K 31/77 | (2006.01) | |
| A61K 31/21 | (2006.01) | |
| A61K 47/34 | (2017.01) | |
| C07C 69/60 | (2006.01) | |

(52) U.S. Cl.
CPC .......... *A61K 31/225* (2013.01); *A61K 9/0019* (2013.01); *A61K 47/60* (2017.08)

(58) Field of Classification Search
CPC ...... A61K 31/21; A61K 31/225; A61K 31/77; A61K 47/34; A61K 47/60; A61K 9/0019; C07C 69/60
See application file for complete search history.

(56) References Cited

U.S. PATENT DOCUMENTS

2017/0290921 A1* 10/2017 Lam .................. A61K 47/60

FOREIGN PATENT DOCUMENTS

| EP | WO 2015/158817 A1 * | 10/2015 | ............. A61P 17/06 |
| EP | WO 2017/108960 A1 * | 6/2017 | ............. C07C 67/08 |

* cited by examiner

*Primary Examiner* — Jeffrey T. Palenik
(74) *Attorney, Agent, or Firm* — McNeely, Hare & War LLP.

(57) ABSTRACT

The present invention comprises compounds of formula (I): where $R^1$ may be PEG or other polymeric moieties. For example, $R^1$ may be repeating PEG units —$(CH_2$—$CH_2$—$O)_n$—, wherein n=1-455. $R^1$ may also be other polymeric moieties of varying sizes and structures, for example, $R^1$ may be poly(glycolide), poly(lactic acid), poly(lactide), poly(caprolactone), poly(lactide-co-caprolactone), poly(lactide-co-glycolide), or poly(lactic acid)-butanol. One or more embodiments of the invention may also relate to injectable pharmaceutical compositions comprising polymer conjugated monomethyl fumarate, and methods for treating relapsing-remitting multiple sclerosis and psoriasis.

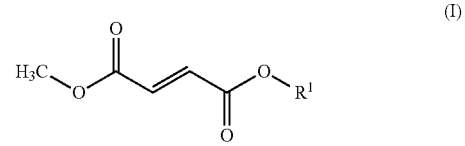

(I)

20 Claims, 6 Drawing Sheets

POLYMERIC COMPOSITIONS OF MONOMETHYL FUMARATE AND THEIR USE IN TREATING RELAPSING REMITTING MULTIPLE SCLEROSIS AND PSORIASIS

CROSS REFERENCE TO RELATED PATENT APPLICATION

This application claims priority to U.S. Patent Application 62/573,103 filed Oct. 16, 2017.

FIELD OF INVENTION

The present invention relates to polymer-conjugated monomethyl fumarate derivatives, and related compositions that treat relapsing-remitting multiple sclerosis and psoriasis.

BACKGROUND OF THE INVENTION

Dimethyl fumarate (DMF) is the active pharmaceutical ingredient of Tecfidera®, a prescription medicine developed for the treatment of relapsing forms of multiple sclerosis (MS), (Tecfidera label) also termed "relapsing-remitting multiple sclerosis" (RRMS). (Gold et al., 2015). Delayed-release Tecfidera capsules were approved by the US Food and Drug Administration (FDA) in 2013 as a first-line oral treatment for RRMS. DMF is also effective against psoriasis and has been approved in Europe for that indication.

DMF has immunomodulatory, anti-inflammatory, and antioxidant properties that are effective in treating MS. It acts by activation of the Nrf2 pathway that induces expression of antioxidant proteins that protect motor neurons and astrocytes against oxidative stress (Scannevin et al., 2012). However, DMF has a very short half-life of 12 minutes after gastrointestinal absorption (Al-Jaderi et al., 2016). DMF is rapidly hydrolyzed by esterase in the gastrointestinal tract to monomethyl fumarate (MMF) prior to entering systemic circulation (eq. 1). The half-life of MMF in circulation is 36 hours (Al-Jaderi et al., 2016), with a $T_{max}$ of about 2.5 hours (Bromprezzi et al., 2015). Thus, DMF is a prodrug of MMF, which is the active metabolite responsible for the pharmacological activity of DMF.

eq. 1

Dimethyl Fumarate

Monomethyl Fumarate

Mechanisms of Action

MMF has been shown to activate the nuclear factor (erythroid-derived 2)-like 2 (Nrf2) transcriptional pathway both in vitro and in vivo in animals and humans (Scannevin et al., 2012). The Nrf2 transcriptional pathway is the main cellular defense system for responding to diverse potentially toxic stimuli, including inflammatory and oxidative stress. By activating this pathway, DMF/MMF reduces inflammatory responses and promotes neuroprotection in both peripheral and central nervous system.

Fumarates including DMF have been shown to be effective in the treatment of psoriasis, by diminishing IL-6 and TGF-α secretion (Ockenfels et al., 1998). DMF inhibits Janus kinas (JAK) signaling and interferes with intracellular protein trafficking. This inhibits the release of pro-inflammatory cytokines, such as IL-12, IL-23, and TNF, whereas the release of anti-inflammatory cytokines, such as IL-10, was increased (Al-Jaderi et al., 2016).

MMF crosses the blood brain barrier and dampens the neuro-inflammation in the central nervous system (Parodi et al., 2015). While studies have established that both DMF and MMF can elicit an antioxidant response in human astrocytes, the assessment of cellular viability under oxidative stress determined that MMF treatment resulted in less toxicity compared to DMF (Scannevin et al., 2012). The cytoprotective effects against oxidative stress of MMF was mediated via the Nrf2 pathway (Scannevin et al., 2012 and Linker et al., 2011). Various studies have identified similar anti-inflammatory, immunomodulatory, neuroprotective, antioxidant, anti-tumor and apoptotic effects for both DMF and MMF in various cell types (Al-Jaderi et al., 2016, Parodi et al., 2015, Linker et al., 2011). Although the mechanism of action of DMF and MMF may not be identical, MMF is the most bioactive metabolite of DMF and all the therapeutic effects of DMF in MS are mediated by MMF. MMF does not deplete glutathione or inhibit mitochondrial and glycolytic function making MMF a better drug. It has also been established that gavage administration of DMF in an experimental autoimmune encephalitis (EAE) mouse model showed a neuroprotective effect through modulation of microglial activation, a critical component of the immunomodulatory cascade in neurodegenerative diseases such as MS (Parodi et al., 2015). The active metabolite in this study was MMF.

Linker et al., 2011 and Scannevin et al., 2012 showed that fumarates exert neuroprotective effects dependent on Nrf2 mediated anti-oxidative pathways. In vitro, MMF-protected cultured neurons and astrocytes from $H_2O_2$ induced cell death. This study found that MMF leads to direct modification of Kelch-like ECH-associated protein 1 (Keap1) at cysteine residue 151. It has been shown that activation of Nrf2 results from covalent modification of free cysteine residues in the Nrf2-binding adaptor protein Keap1 that targets Nrf2 for ubiquitin-mediated degradation leading to suppression of Nrf2 function. Modification of cysteine 151 by electrophiles renders Keap1 incapable of interacting with Nrf2 and thus leads to stabilization of Nrf2, its accumulation in the nucleus and activation of induction of Nrf2-dependent expression of antioxidant and cytoprotective genes.

Parodi et al. (2015) showed that an anti-inflammatory effect of MMF is caused by switching the molecular and functional phenotype of activated microglia from classically activated, pro-inflammatory type to alternatively activated, neuroprotective one, through activation of the hydroxycarboxylic acid receptor 2 (HCAR2). Activation of HCAR2 by MMF leads to deacetylation, and thereby inhibition of NF-κB via the AMPK/SIRT1 axis triggered by the increase in intracellular calcium. Blockade of HCAR2 with an anti-HCAR2 antibody reversed the effect of MMF on the relevant pathway, demonstrating that MMF signals through HCAR2 to modulate the expression of inflammatory molecules dependent upon NF-κB activation. This demonstrates a possible role of DMF and its metabolite MMF in neurodegenerative diseases such as MS.

Taken together, these studies, and others, demonstrate viable mechanisms by which fumarates, in particular the active metabolite MMF, can favorably alter the course of the disease process in MS. Because of the anti-inflammatory, anti-oxidant, and immune modulatory properties, fumarates have also been investigated for therapy of autoimmune conditions including psoriasis and inflammatory lung diseases like asthma, neuro-inflammatory and neurodegenerative conditions such as relapsing remitting and progressive forms of multiple sclerosis, Parkinson's disease, Alzheimer's disease as well as ischemic stroke for post-Ischemic recovery (Seidel et al., 2009, Strassburger-Krogias et al., 2014, Yao et al., 2016, Ahuja et al., 2016, Paraiso et al., 2018).

Side Effects of DMF/MMF

Tecfidera delayed release DMF capsules for oral administration has several deleterious side effects including, allergic reactions, progressive multifocal leukoencephalopathy (PML, a rare brain infection leading to death or severe disability), decrease in white blood cell count, and liver problems, in turn causing exhaustion, loss of appetite, abdominal pain, dark or brown (tea color) urine, and jaundice. The most common side effects are flushing and stomach problems such as fullness, bloating, diarrhea, upper abdominal cramps, flatulence, and nausea. The GI side effects can be severe and reached an incidence up to 38% for treatment groups in clinical trials (Bombrezzi et al., 2015).

In addition, the pharmacokinetics of oral delayed release DMF capsules has several problems. The $C_{max}$ and AUC variations are large (Shiekh et al., 2013), and were also found to be undesirably variable particularly after food (Litjens et al., 2004).

Alternative Formulations

In view of the efficacy of oral DMF in RRMS, researchers have been working to find alternative formulations of DMF/MMF for the treatment of RRMS in an attempt to alleviate some of these harmful side effects. For example, Forward Pharma is developing a delayed release proprietary DMF formulation (FP187). Xenoport is developing an MMF prodrug, XP23829. Alkermes is developing ALKS8700, an MMF prodrug. However, these drugs may still cause significant side effects. For example, XenoPort reported that its XP23829 prodrug caused frequent gastrointestinal-related side effects during its phase 2 clinical trial.

SUMMARY OF THE INVENTION

In order to address the aforementioned shortcomings in the administration of dimethyl fumarate (DMF), including adverse events and highly variable pharmacokinetics on oral administration, the present invention provides polymer-conjugated monomethyl fumarate (MMF) derivatives and related compositions or formulations. For example, one or more embodiments of the invention relate to injectable PEGylated MMF derivatives that offer improved chemical and pharmaceutical properties compared to DMF or MMF alone for the treatment RRMS. The present invention comprises compounds of formula (I), where $R^1$ may comprise PEG or other polymeric moieties. For example, $R^1$ may comprise repeating PEG units —$(CH_2—CH_2—O)_n$—, wherein n=1-455. $R^1$ may also comprise other polymeric moieties of varying sizes and structures, for example, poly(glycolide), poly(lactic acid), poly(lactide), poly(caprolactone), poly(lactide-co-caprolactone), poly(lactide-co-glycolide), or poly(lactic acid)-butanol.

One or more embodiments of the invention may also relate to pharmaceutical compositions, for example injectable pharmaceutical compositions, comprising polymer conjugated monomethyl fumarate according to formula (I). The invention also relates to methods of treating RRMS and psoriasis for example through controlled release injectable compositions of polymer conjugated MMF, thus avoiding local high concentrations of the drug within the gastrointestinal tract upon oral administration and reducing gastrointestinal side effects.

DETAILED DESCRIPTION

In an embodiment, the present invention provides a monomethyl fumarate (MMF) derivative useful for the treatment of relapsing-remitting multiple sclerosis (RRMS) that alleviates the side effects of oral dimethyl fumarate (DMF), and provides stable injectable compositions that have superior pharmacokinetic properties. In an embodiment, this invention provides an MMF-polymer conjugate according to formula (I)

(I)

where $R^1$ may comprise polyethylene glycol (PEG) or other polymeric moieties. In an embodiment, $R^1$ may comprise repeating PEG units —$(CH_2—CH_2—O)_n$—, wherein n=1-455. $R^1$ may also comprise other polymeric moieties of varying sizes and structures, for example, poly(glycolide), poly(lactic acid), poly(lactide), poly(caprolactone), poly(lactide-co-caprolactone), poly(lactide-co-glycolide), or poly(lactic acid)-butanol.

PEG is supplied in various molecular weight grades, for example, PEG-1000 has a molecular weight of about 1000, which may be stated as between approximately 950 and 1050. In an embodiment, this invention uses PEG with a molecular weight of 400 (n=8-10), 1000 (n=21-25), 2000 (n=43-48), 3000 (n=65-71), or 5000 (n=112-117).

In an embodiment, other polymers may be useful in this invention, including poly(glycolide), poly(lactic acid), poly(lactide), poly(caprolactone), poly(lactide-co-caprolactone), poly(lactide-co-glycolide), or poly(lactic acid)-butanol.

In an embodiment, the polymer of this invention may be a straight chain, a branched chain, a substituted chain, and unsubstituted chain, or globular.

Advantages of pharmaceutical compositions comprising PEGylated, or other polymer conjugated MMF derivatives disclosed herein include, for example: increased bioavailability at lower doses; predictable drug-release profile over a defined period of time following each injection; better patient compliance; ease of application; improved systemic availability by avoidance of first-pass metabolism; reduced dosing frequency (i.e., fewer injections) without compromising the effectiveness of the treatment; decreased incidence of side effects; and overall cost reduction of medical care.

Polyethylene Glycol (PEG) and PEGylation

Polyethylene glycol (PEG) can be linked via an ester linkage to drug molecules to exert desirable effects on a molecule that may be immunoreactive or rapidly metabolized. PEG is non-toxic, non-immunogenic, non-antigenic, highly soluble in water and FDA approved. PEG-drug conjugates have several advantages: a prolonged residence in body, a decreased degradation by metabolic enzymes and a reduction or elimination of protein immunogenicity. The covalent attachment of PEG to a drug can increase its hydrodynamic size (size in solution), which prolongs its circulatory time by reducing renal clearance (Knop et al., 2010, Veronese et al., 2005 and Harris et al., 2003).

The linkage of PEG to drug molecules is called "PEGylation." Several PEGylated drugs have been approved, including peptide and non-peptide drugs. A few examples of PEGylated drugs include: Pegaptanib (brand name MACUGEN®); Antihemophilic Factor (Recombinant), PEGylated, (brand name ADYNOVATE®), and peginterferon beta-1a (brand name PLEGRIDY®)).

Preparation of Monomethyl Fumarate-PEG Conjugates

A synthetic route to monomethyl fumarate-polyethylene glycol (MMF-PEG) conjugates is shown in eq. 2.

Eq. 2

MMF-PEG1000; n = 22-23
MMF PEG2000; n = 45-47

The PEG conjugates were produced by a coupling reaction between PEGs and MMF in presence of N-(3-Dimethylaminopropyl)-N'-ethylcarbodiimide hydrochloride (EDC) and dimethyl amino pyridine (DMAP) (see experimental section). Following purification, the products were confirmed by NMR and mass spectroscopic analysis.

Figure 1A:
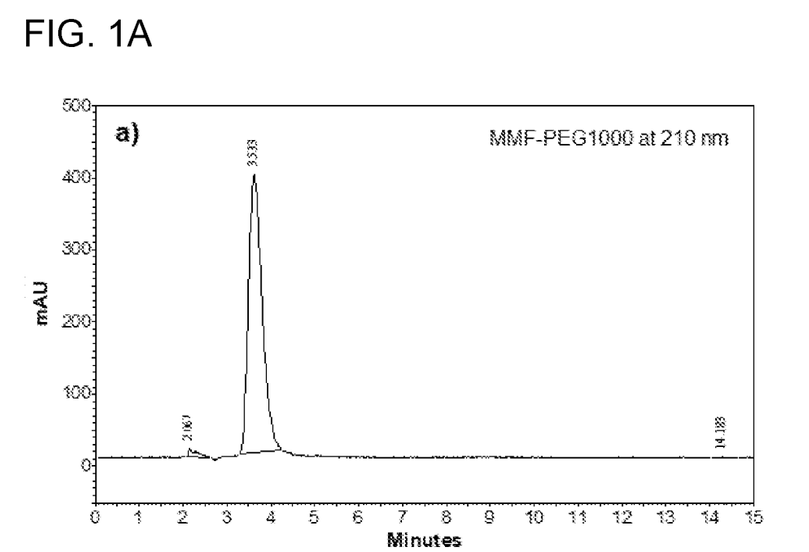
FIG. 1A shows an HPLC chromatogram of MMF-PEG1000 monitored with a 210 nm UV detector (retention time 3.53 min). The retention time of MMF is 2.11 min.
Figure 1B:
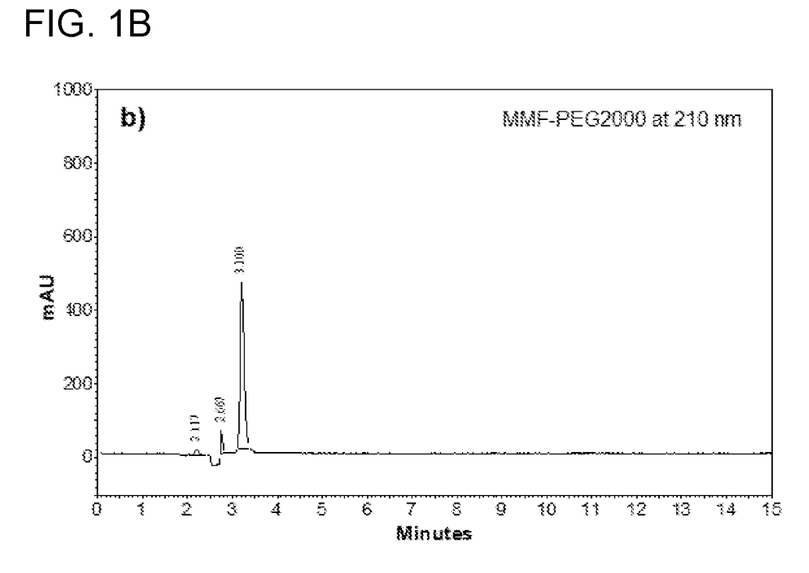
FIG. 1B shows an HPLC chromatogram of MMF-PEG 2000 monitored with a 210 nm UV detector (retention time 3.10 min). The retention time of MMF is 2.11 min and the peak at 2.66 min is from mobile phase.

The purity of the final MMF-PEG conjugates was confirmed by reverse-phase HPLC monitored at 210 and 260 nm, where no such significant amounts of starting material as well as impurities present (FIGS. 1A and 1B). The percentage purity of the MMF-PEG conjugates are 97.7% (1.0 kDa PEG, retention time 3.53 min) and 96.5% (2.0 kDa PEG, retention time 3.10 min) at 210 nm. The retention time of MMF is 2.11 min and the absence of MMF peak at 260 nm confirm the formation of the conjugates in both cases.

Figure 2A:
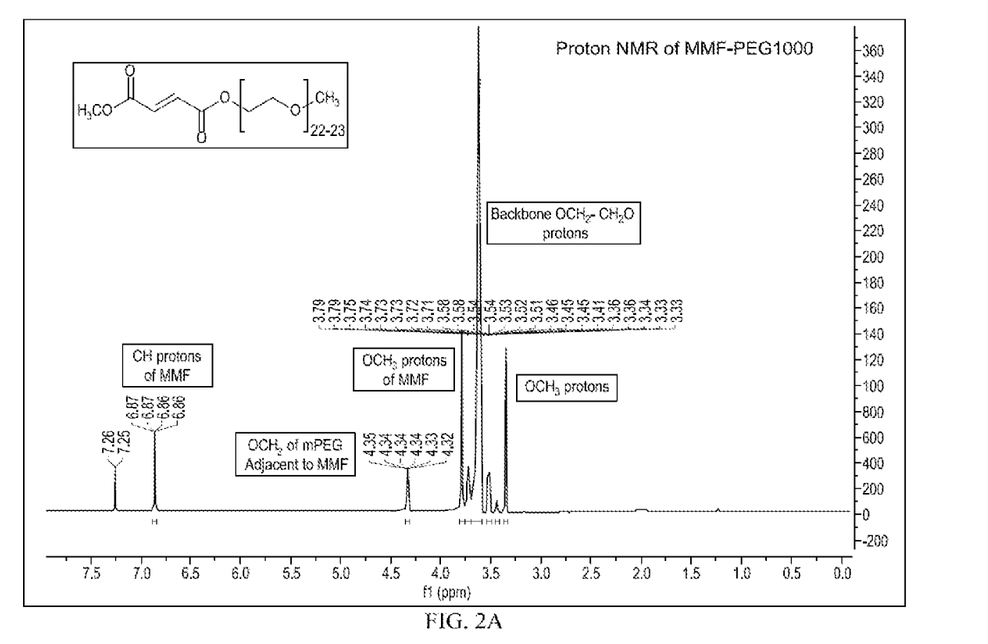
FIG. 2A shows the proton NMR spectra of MMF-PEG1000 conjugate. Deuterated chloroform (CDCl3) was used as solvent.
Figure 2B:
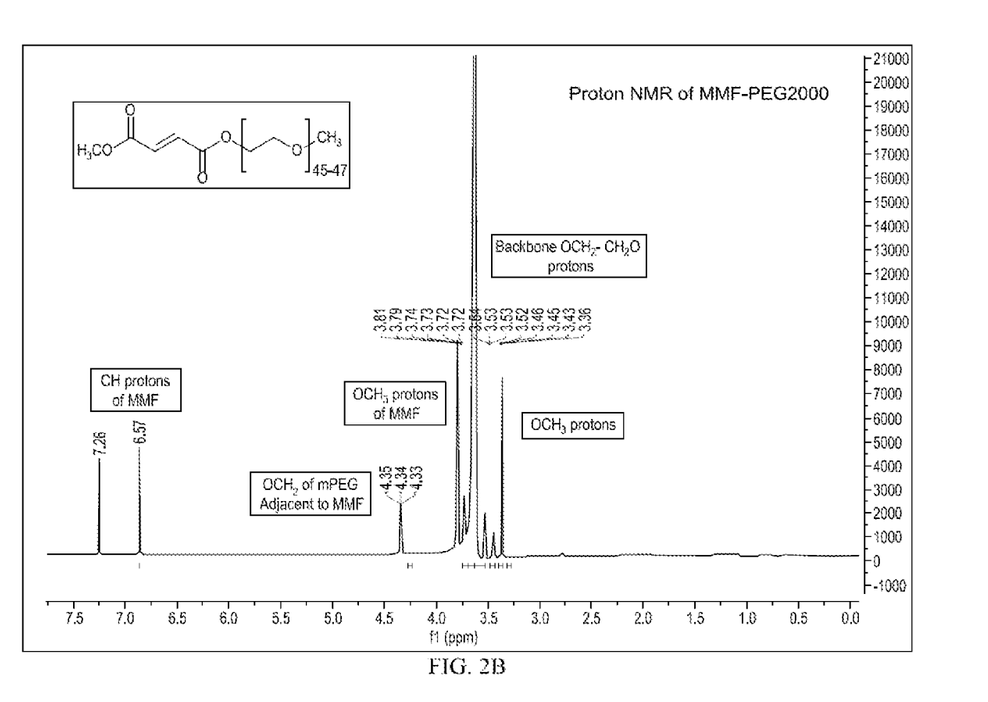
FIG. 2B shows the proton NMR spectra of MMF-PEG2000 conjugate. Deuterated chloroform (CDCl3) was used as solvent.

In the $^1H$ NMR of MMF-PEG1000 conjugate shown in FIG. 2A, the presence of a characteristic peak at 4.35 ppm for $OCH_2$ group of PEG confirmed the formation of ester bond between MMF and PEG. Additionally, other peaks related to both chemical entities are present such as singlet at 3.79 ppm for methoxy group of MMF, singlet at 3.33 ppm for methoxy group of PEG, multiplets at 3.44-3.75 for the backbone $OCH_2$ groups of PEG, and a singlet at 6.87 ppm for two protons (CH═CH) of MMF confirmed the formation of the conjugate. In a similar manner, the structure of MMF-PEG2000 conjugate was established shown in FIG. 2B.

Figure 3A:
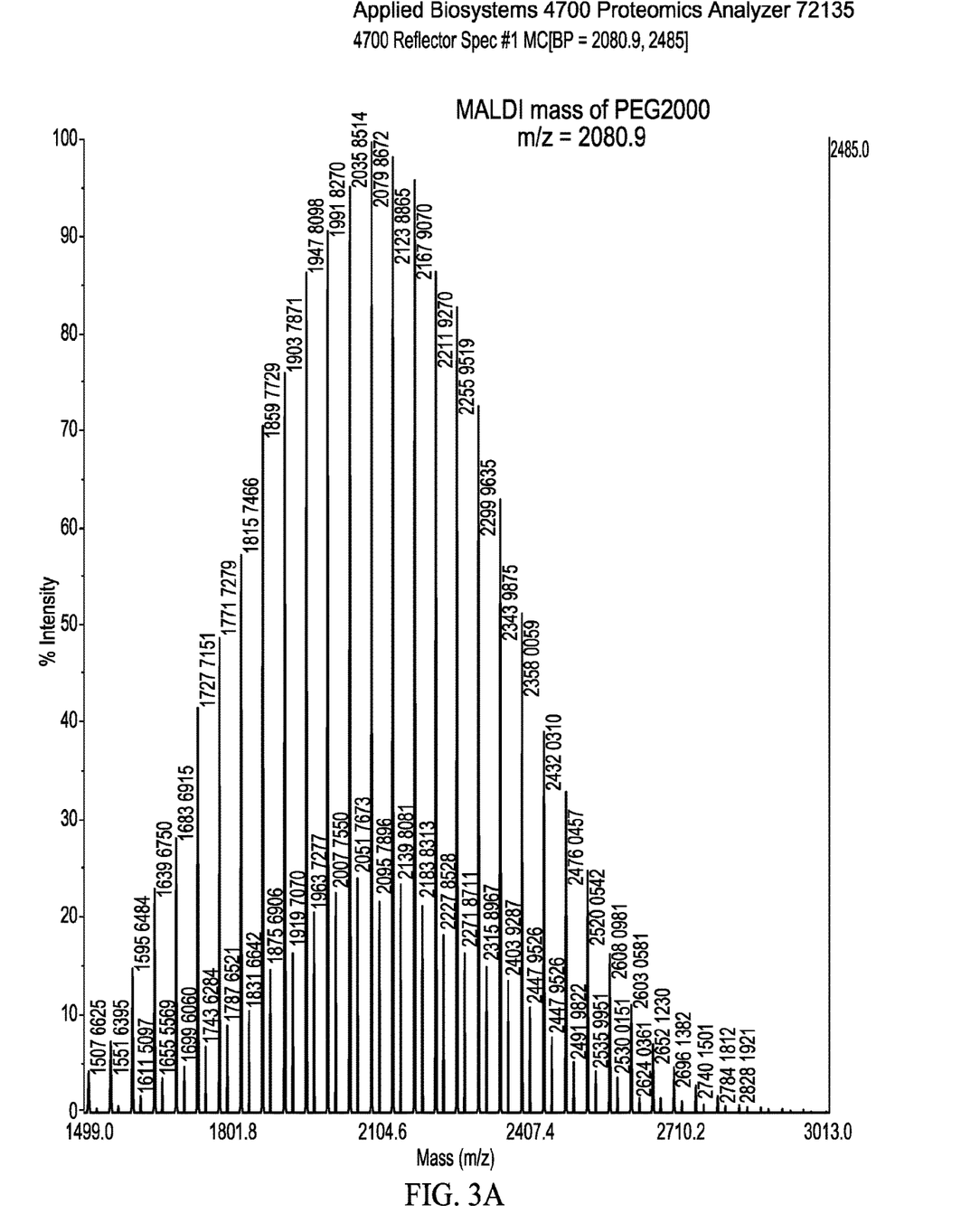
FIG. 3A. MALDI TOF mass spectrum of PEG2000 (m/z=2080.9).
Figure 3B:
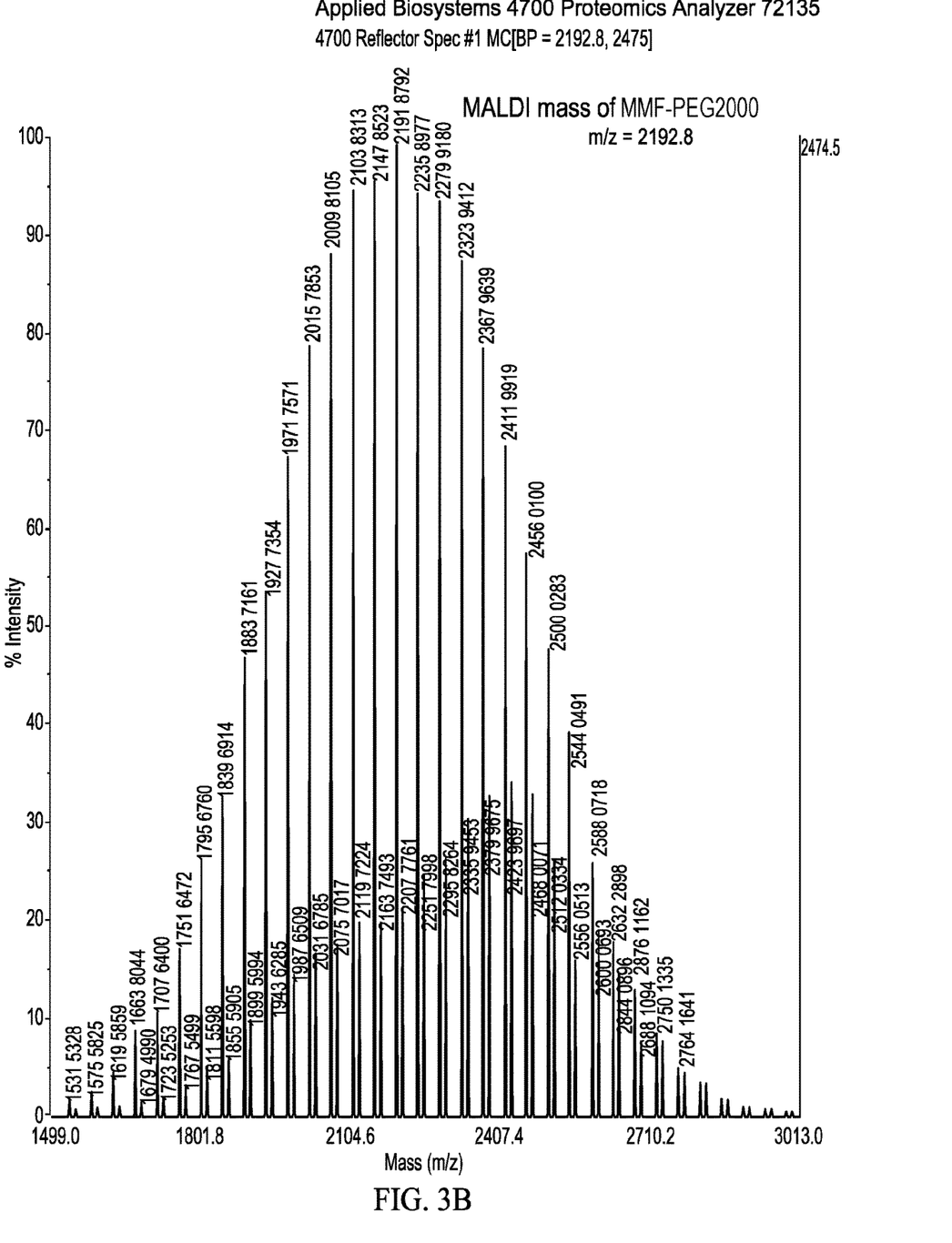
FIG. 3B. MALDI TOF mass spectrum of MMF-PEG2000 conjugate (m/z=2192.8).

The molecular weight of both MMF-conjugates was evaluated using MALDI TOF mass spectroscopy. The molecular weight of the MMF-PEG1000 conjugate is 1223.5 g/mol when we used PEG1000 as starting materials. The average molecular weight of PEG1000 is 1039.4 g/mol which implies that there are 22-23 $OCH_2$—$CH_2O$ repeating units present in the PEG chain. Based on molecular weights of PEG1000 and corresponding conjugate, it was determined that one MMF molecule attached to the PEG. This finding is in good agreement with the NMR analysis of the conjugate. In a similar way the structure of MMF-PEG2000 conjugate (m/z=2192.8 g/mol) was established. A representative MALDI TOF spectra of PEG2000 and MMF-PEG2000 conjugate are shown in FIGS. 3A and 3B respectively. In both proton NMR and in MALDI TOF mass cases, it was established that approximately one molecule of MMF reacted with the corresponding PEG molecules.

In-Vitro Drug Release Study of the MMF-PEG Conjugates

In vitro MMF release characteristics of the inventive MMF-PEG conjugates were studied to investigate their stability in physiologically relevant solutions such as PBS (pH 7.4) and in human plasma. 80% Human plasma was used to in the study simulate the biological conditions of intravenous injection.

Drug Release Study in PBS: A drug release study of the MMF-PEG conjugates was performed in 0.1 M phosphate buffer (pH 7.4) at 37° C. A concentration of 3 mg/mL of the conjugate was placed in a water bath and the temperature of the bath was maintained at 37° C. with constant mixing. Samples were collected at appropriate time points and lyophilized using liquid nitrogen. The MMF-PEG conjugates along with released MMF were extracted from the lyophilized powder using acetonitrile and the samples were analyzed in reverse-phase HPLC. The peaks of MMF-PEG conjugates and MMF were monitored at 210 and 260 nm respectively. Since the MMF also further degrades, peak area of MMF-PEG conjugate was used for the analysis.

Figure 4:
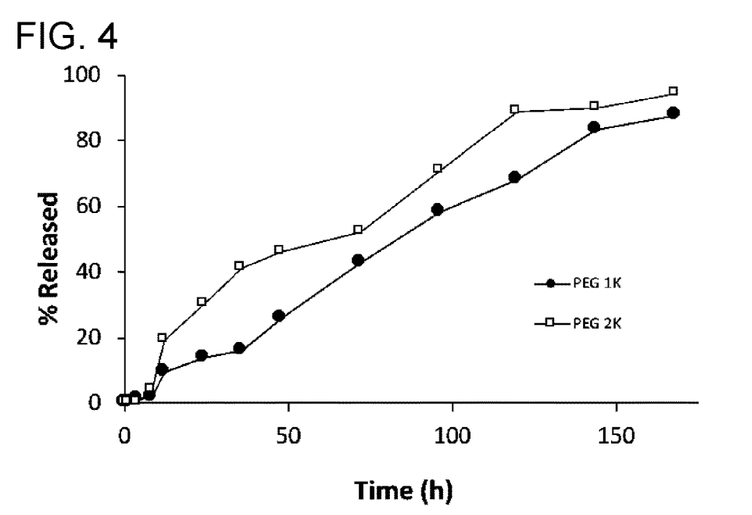
FIG. 4 shows the release kinetics of MMF-PEG conjugates (1 kDa and 2 kDa) in PBS.

The results of the study of MMF-PEG 1000 and 2000 conjugates in PBS is shown in FIG. 4. In PBS, both the conjugates released the drug in a steady manner and the release pattern is nearly zero order. Approximately 90% of the drug payload was released in 7 days in both cases with no initial burst. The drug from PEG1000 conjugate is releasing much slower than PEG2000 conjugate. In HPLC the released MMF was monitored at 260 nm. After 4 days, the ester bond of MMF of other end started degrading resulted to a di-acid form of monomethylfumarate.

Drug Release Study in Plasma: Another MMF release study from the MMF-PEGylated conjugates (3 mg/mL) was performed using human pooled plasma diluted to 80% with 0.1 M PBS in a water bath (Dual-action shaker; Polyscience) at 37° C., collecting 200 μL aliquots of the sample at appropriate intervals. The protein was precipitated using 2 M trichloroacetic acid, cold acetonitrile was added, centrifuged, filtered, and stored at −80° C. for HPLC analysis. Different solvents may be used to extract the drug conjugates as well as the released drug from the plasma solution. Each sample was analyzed using HPLC, and the drug release was calculated using a calibration graph. DMF was used as the reference drug for this study.

Figure 5:
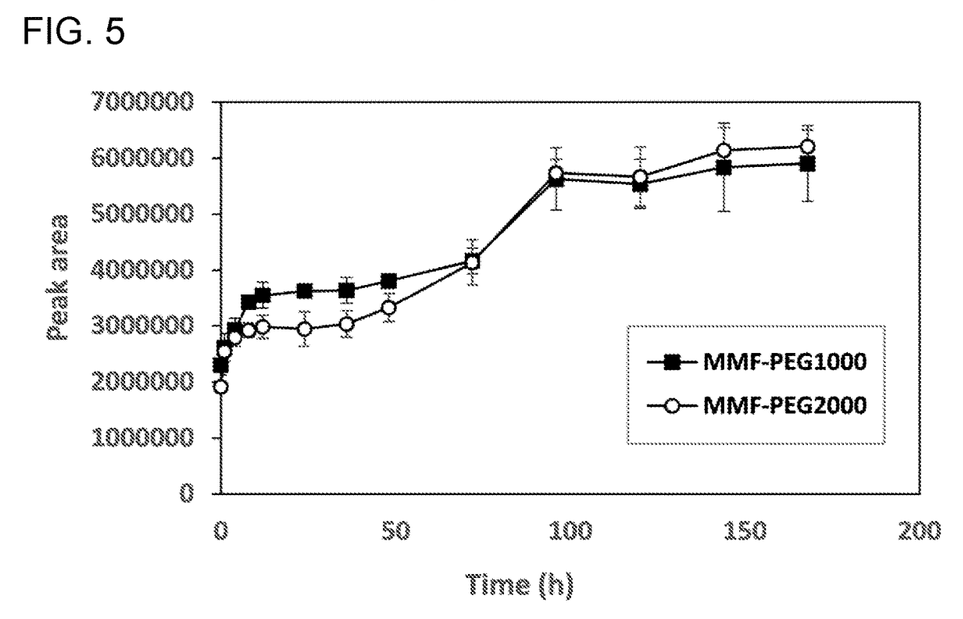
FIG. 5 shows the release kinetics of MMF-PEG conjugates (1 kDa and 2 kDa) in 80% human plasma.

The results of the plasma study are shown in FIG. 5. In human plasma, the extent of release was relatively higher for both MMF-PEG conjugates, compared to PBS at the same time point. This type of release pattern is expected because of the presence of enzymes (e.g. esterase) which can specifically cleave the ester bond much faster than in case of PBS. Both conjugates are very similar, with the PEG1000 conjugate showing slightly faster release during the initial time points. There are burst release of MMF in case of plasma in initial point (31% at 0 h in case of 2 kDa and 39% at 0 h in case of 1 kDa). Similar to PBS release, the drug started degrading after the 4th day, the peak for the degradation product was very prominent compared to the drug peak. The peak area corresponds to the degraded product was included in the calculation. Based on the plasma release profile, a slow release of the drug from the conjugates in vivo is expected.

Pharmacokinetics in Mice

A pilot pharmacokinetics study was done to determine the route of administration and best possible corresponding dose to get the therapeutic level of MMF in blood. MMF conjugates (500 μg of MMF equivalent) were injected intravenous (IV) and subcutaneous (SC) in 5-6 weeks old BALB-NeuT mice and MMF concentration was determined with HPLC up to day 7. The MMF concentration were increased from 1 h to 24 h and roughly 10% of the MMF was detected in blood plasma at 24 h in both cases. The drug concentration steadily decreased until day 7 in both cases, and MMF concentration in the plasma was in the range of 11-18 μg/mL on day 7 in SC and IV routes of administration. The MMF concentrations in the plasma are higher in case of PEG2000 as compared to PEG1000 in SC and IV route. The peak plasma concentrations of MMF were higher following SC route compared to IV route of injection at all time points.

Since the MMF concentration in blood is reported for Tecfidera (Tecfidera label), our aim was to match the same drug concentration in the blood in mice. The average $C_{max}$ value of MMF in blood was 2.74 μg/mL (360 mg single dose) and 2.15 μg/mL (240 mg single dose) when Tecfidera was administered to healthy volunteers (FDA DMF Pharmacology Review). Dosing MS patients with 240 mg BID of Tecfidera resulted in a mean $C_{max}$ of 1.87 μg/mL and the AUC was 8.21 mg·hr/L (Tecfidera label). The Biogen pharmacokinetics of Tecfidera showed high inter-subject variability with respect to the $C_{max}$ value.

To achieve the required MMF concentration in the blood, 150 μg of MMF equivalent conjugate (PEG2000) was injected IV and SC routes and blood samples were collected up to day-10 and MMF concentrations were analyzed. The MMF levels were highest at day-1 in both cases and gradually decreased till day-7. However, no MMF was observed at 240 h (day 10) in either route of administration. At day-7 the MMF concentrations were 2.00 μg/mL (IV) and 2.36 μg/mL (SC). In the above findings the MMF concentration observed were comparative to those observed with therapeutic dose of oral Tecfidera 240 mg twice daily.

A full-scale pharmacokinetics study was done using MMF conjugate (PEG2000) with SC route of administration. Two doses strength of the MMF conjugate were injected (100 and 150 μg of MMF equivalent) subcutaneous in 5 weeks BALB/C mice (n=5) and the MMF concentrations were determined up to Day 10. The objective of the study was to determine the pharmacokinetics of active drug MMF following subcutaneous injection, with the goal of achieving plasma concentrations in the 1-10 μg/mL range. The MMF concentration was determined with HPLC and PK parameters such as $t_{1/2}$, $C_{max}$, $T_{max}$, AUC, CL (clearance), and Vd (volume of distribution) were calculated.

Figure 6:
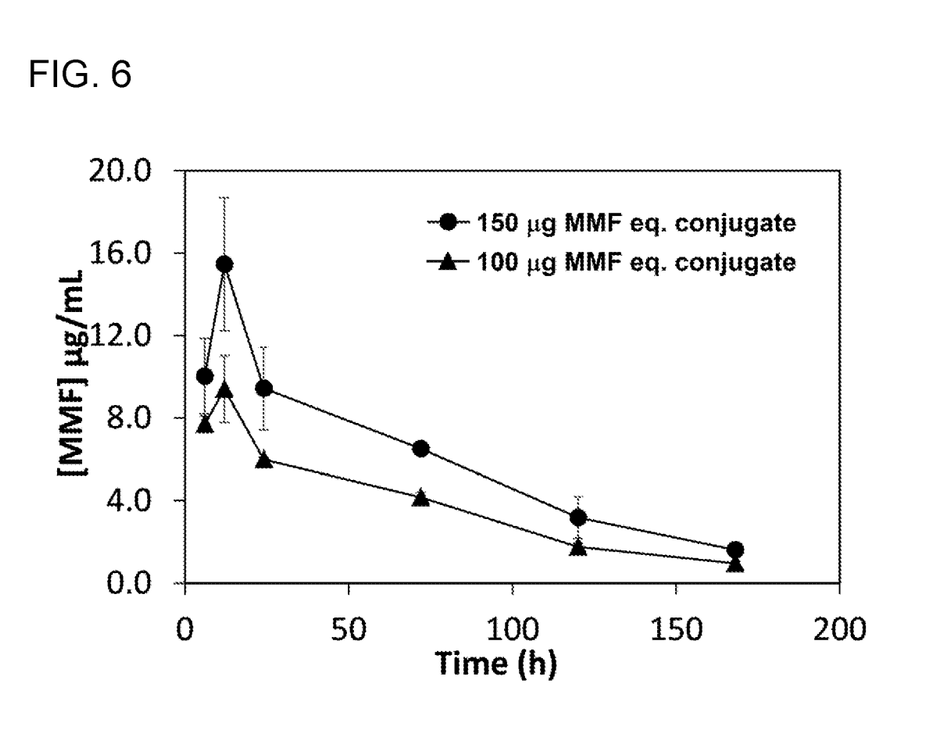
FIG. 6 shows a plot of MMF pharmacokinetics, showing plasma concentration vs. time following subcutaneous administration of MMF-PEG2000 conjugate in mice.

The pharmacokinetics results are shown in FIG. 6. It was observed that the 100 μg of MMF equivalent conjugate dose resulted in MMF plasma concentrations ranging from 7.7 μg/mL (6 h) to 1 μg/mL (day 7) with Cmax concentration at 12 h (9.4 μg/mL). In case of 150 μg equivalent of MMF, the plasma concentrations were ranging from 15.5 to 1.67 μg/mL when monitored starting from 6 h to day-7. The MMF was not detected at day-10 in either dose groups. The results suggest that there is a good correlation between administered dose and plasma concentrations, at least in this dose range. Other pharmacokinetic non-dose dependent parameters such as the volume of distribution, clearance and half-life showed good concordance for the two doses.

Compositions of MMF-Polymer Conjugates

In an embodiment, this invention is directed to an injectable dosage form, adapted for administration to a patient parenterally including subcutaneous, intramuscular, intravenous or intradermal injection. Pharmaceutical compositions adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The compositions may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

Materials and Methods

Materials: N-(3-Dimethylaminopropyl)-N'-ethylcarbodiimide hydrochloride (EDC), 4-(Dimethylamino) pyridine (DMAP) was purchased from Sigma-Aldrich (St. Louis, Mo., USA). mPEG-OH (1 kDa and 2 kDa) were procured from Creative PEGworks (Chapel Hill, N.C., USA). ACS grade dimethylformamide (DMF), dichloromethane (DCM), chloroform and methanol were obtained from Fisher Scientific. Regenerated cellulose (RC) dialysis membrane with molecular weight cut-off 1000 Da was obtained from Spectrum Laboratories, Inc. (Rancho Dominguez, Calif., USA). Deuterated chloroform ($CDCl_3$) was purchased from Cambridge Isotope Laboratories, Inc. (Andover, Mass., USA).

Preparation of MMF-PEG1000 conjugate: Monomethyl fumarate (0.7 gm, 5.52 mmol) was dissolved in 30 mL of DCM/dry dimethylformamide (9:1, v/v) in a 100 mL two neck flask under nitrogen environment and EDC (1.4 gm, 9.2 mmol) and DMAP (0.03 g, 0.27 mmol) were added to it and stirred the reaction mixture for half an hour in an ice bath. Finally the mPEG-OH (1 kDa, 1.0 g, 0.92 mmol) was added dissolved in 10 mL of dry DCM and the reaction mixture was stirred for 24 h at room temperature. The solvent was evaporated at room temperature under vacuum. The crude product was purified using column chromatography over silica gel (60-120 mesh). The mixture of solvents was used (0.75% methanol in dichloromethane) as eluent afforded 0.52 g of MMF-PEG1000 conjugate (47% yield and Rf=0.6, 5% methanol in DCM). The final MMF-PEG1000 conjugate was characterized by reverse-phase HPLC, proton NMR and MALDI-TOF mass spectroscopy. $^1$H NMR (400 MHz, $CDCl_3$): δ 3.33 (s, 3H, $OCH_3$ of mPEG), 3.44-3.75 (m, backbone $OCH_2CH_2O$ of mPEG), 3.79 (s, 3H, $OCH_3$ of MMF), 4.35 (m, 2H, $OCH_2$ of mPEG adjacent to MMF), 6.87 (m, 2H, —CH═CH— of MMF).

Preparation of MMF-PEG2000 conjugate: Monomethyl fumarate (0.35 g, 2.74 mmol) was dissolved in 30 mL of dry DCM/dry DMF (9:1, v/v) under nitrogen condition in an ice bath; and EDC (0.69 g, 4.5 mmol) and DMAP (0.01 g, 0.13 mmol) were added to it. The reaction mixture was stirred for 30 min and mPEG-OH (2 kDa, 1 g, 0.45 mmol) dissolved in 10 mL of dry DCM was added to the reaction mixture. The resulting reaction mixture was stirred for 24 h at room temperature. The solvent was removed under reduced pressure at room temperature and the obtained crude product was dialyzed in DI water using dialysis membrane (MWCO 1 kDa) for 36 h. The obtained solution was lyophilized to get 0.72 g of MMF-PEG2000 conjugate (68% yield). The final MMF-PEG2000 conjugate was characterized by HPLC, $^1$H NMR and MALDI-TOF mass spectroscopy. $^1$H NMR (400 MHz, $CDCl_3$): δ 6.87 (s, 2H, —CH═CH— of MMF), 4.35 (m, 2H, $OCH_2$ of mPEG adjacent to MMF), 3.81 (s, 3H, $OCH_3$ of MMF) 3.43-3.76 (m, backbone $OCH_2CH_2O$ of mPEG), 3.36 (s, 3H, $OCH_3$ of PEG).

Nuclear Magnetic Resonance (NMR) Spectroscopy: NMR spectra of final conjugates as well as starting materials was recorded on a Varian Spectrometer (400 MHz). Tetramethylsilane (TMS) was used as internal standard and deuterated chloroform ($CDCl_3$) was used as solvents to dissolve the conjugates.

Matrix-Assisted Laser Desorption Ionization-Time-of-Flight (MALDI-TOF) Mass Spectrometry: MALDI-TOF mass spectra was recorded in a AB-Sciex 5800 MALDI/TOF-MS instrument operating in the reflector mode. 2,5 Dihydroxybenzoic acid (DHB) was used as matrix and cytochrome c (MW 12361 g/mol) was used as external standard. The matrix solution was prepared by dissolving 20 mg of matrix in 1 mL of deionized water/ACN (0.1% TFA; 1:1). Samples were prepared by mixing 10 μL of conjugates (2 mg/mL in methanol) with 100 μL of matrix solution, and subjected 1 μL of sample mixture onto the MALDI plate. The samples were allowed to air-dry at room temperature and used for analysis.

High performance liquid Chromatography (HPLC): The MMF-PEG conjugates were analyzed by system gold HPLC instrument (Beckman Coulter. Inc. Brea, Calif.) equipped with binary pump, UV detector, and autosampler interfaced with 32 Karat software. Acetonitrile:phosphate buffer pH 6.8 (75:25, v/v) in gradient flow (1 mL/min) was used as the mobile phase and chromatograms were monitored at 210 nm. Supelcosil LC-18 column with 5 μm particle size, 25 cm length, 4.6 mm internal diameter was used for the analysis.

Drug Release Study in PBS: The drug release study of the MMF-PEG conjugates was performed in 0.1 M phosphate buffer (pH 7.4) at 37° C. A concentration of 3 mg/mL of the conjugate was placed in a water bath and the temperature of the bath was maintained at 37° C. with constant mixing. Samples were collected at appropriate time points and lyophilized sing liquid nitrogen. The MMF-PEG conjugates along with released MMF were extracted from the lyophilized powder using acetonitrile and the samples were analyzed in reverse-phase HPLC. The peaks of MMF-PEG conjugates and MMF were monitored at 210 and 260 nm respectively. Since the MMF also further degrades, peak area of MMF-PEG conjugate was used for the analysis.

Drug Release Study in Plasma: The MMF-PEG conjugates (3 mg/mL) were incubated in human pooled plasma diluted to 80% with 0.1 M PBS with constant mixing in water bath at 37° C. The plasma samples were collected at periodic intervals and lyophilized using liquid nitrogen. Both MMF-PEG conjugates and released MMF were extracted from the lyophilized samples using methanol. The samples were analyzed by reverse-phase HPLC using acetonitrile:phosphate buffer pH 6.8 (75:25) as mobile phase at 210 and 260 nm. The peak area of MMF was used for the analysis.

To obtain a standard plot, MMF was accurately weighed and spiked in blank plasma. Stock solution of 5000 μg/mL was prepared and was further diluted to 250, 125, 62.5, 31.25, 15.6, 7.8, 3.9, 1.9 and 0.9 μg/mL (n=2). A standard plot was obtained with regression equation y=260748x+371377 (Correlation coefficient=0.9976). Proteins were precipitated using 2M trichloroacetic acid and centrifuged at 3000 rpm at 4° C. for 10 min. The supernatant was transferred into a fresh 1.5 ml tubes and freeze dried. MMF was extracted from freeze dried samples using acetonitrile and centrifuged at 3000 rpm at room temperature for 10 min. Supernatant was analyzed by HPLC using acetonitrile:phosphate buffer pH 6.8; 75:25, as a mobile phase. The calibration plots were constructed between the absorbance values and the respective concentration values. MMF peak was monitored at 210 nm.

Dose and route determination studies of the MMF conjugates in mice. A pharmacokinetic pilot study was performed with five to six-week-old BALB-NeuT mice (n=2). Each animal was injected intravenously or subcutaneously with a single dose of MMF-PEG conjugates (500 μg and 150 μg of MMF equivalent conjugates) in a total 200 μL of PBS. Mice were euthanized at different time intervals post-injection and blood samples were withdrawn via cardiac puncture. Plasma were collected from the samples by centrifugation at 3000 rpm at 4° C. for 20 min. The proteins were precipitated using 2M trichloroacetic acid and centrifuged at 3000 rpm at 4° C. for 10 min. The supernatant was transferred into fresh 1.5 ml tubes and freeze dried. The drug was extracted using acetonitrile and centrifuged at 3000 rpm at room temperature for 10 min. Supernatant was analyzed by HPLC using acetonitrile:phosphate buffer pH 6.8; 75:25, as a mobile phase. Peak area of MMF was used for the analysis.

A full-scale pharmacokinetic study was performed with 5-week old BALB/c mice (n=5). Each animal was injected subcutaneously with a single dose of MMF-PEG2000 conjugate (100 µg and 150 µg of MMF equivalent conjugate) in a total 200 µL of PBS. Mice were euthanized at 6, 12, 24, 72, 120, 168, and 240 h post-injection and blood samples were withdrawn via cardiac puncture. Plasma were collected from the samples by centrifugation at 3000 rpm at 4° C. for 20 min. The proteins were precipitated using 2M trichloroacetic acid and centrifuged at 3000 rpm at 4° C. for 10 min. The supernatant was transferred into fresh 1.5 ml tubes and freeze dried. The drug was extracted using acetonitrile and centrifuged at 3000 rpm at room temperature for 10 min. Supernatant was analyzed by HPLC using acetonitrile:phosphate buffer pH 6.8; 75:25, as a mobile phase. Peak area of MMF was used for the analysis.

ABBREVIATIONS

| | |
|---|---|
| Dimethyl fumarate (also used for N,N-dimethyl formamide) | DMF |
| Food and Drug Administration | FDA |
| Matrix Assisted Laser Desorption/Ionization | MALDI |
| Monomethyl fumarate | MMF |
| Multiple sclerosis | MS |
| Nuclear Magnetic Resonance | NMR |
| Phosphate Buffered Saline | PBS |
| Polyethylene glycol | PEG |
| relapsing-remitting multiple sclerosis | RRMS |
| N-(3-Dimethylaminopropyl)-N'-ethylcarbodiimide hydrochloride | EDC•HCl |
| 4-(Dimethylamino)pyridine | DMAP |
| Dichloromethane | DCM |

REFERENCES

Ahuja M, Ammal Kaidery N, Yang L, Calingasan N, Smirnova N, Gaisin A, Gaisina I N, Gazaryan I, Hushpulian D M, Kaddour-Djebbar I, Bollag W B, Morgan J C, Ratan R R, Starkov A A, Beal M F, Thomas B "Distinct Nrf2 Signaling Mechanisms of Fumaric Acid Esters and Their Role in Neuroprotection against 1-Methyl-4-Phenyl-1,2,3,6-Tetrahydropyridine-Induced Experimental Parkinson's-Like Disease." J Neurosci. (2016) 36(23): 6332-51. doi:10.1523/JNEUROSCI.0426-16.2016.

Al-Jaderi Z and Maghazachi A A "Utilization of Dimethyl Fumarate and Related Molecules for Treatment of Multiple Sclerosis, Cancer, and Other Diseases." Front. Immunol. (2016) 7:278. doi:10.3389/fimmu.2016.00278.

Bomprezzi, R "Dimethyl fumarate in the treatment of relapsing-remitting multiple sclerosis: an overview." Therapeutic advances in neurological disorders (2015) 8(1):20-30. doi:10.1177/1756285614564152.

FDA Center for Drug Evaluation and Research, Clinical Clinical Pharmacology and Biopharmaceutics Review, Application No. 204063Orig1s000, Dimethyl Fumarate Feb. 12, 2013.

Gold R, Kappos L, Arnold D L, Bar-Or A, Giovannoni G, Selmaj K, Tornatore C, Sweetser M T, Yang M, Sheikh S I, Dawson K T; DEFINE Study Investigators "Placebo-controlled phase 3 study of oral BG-12 for relapsing multiple sclerosis." New England Journal of Medicine (2012) 367(12):1098-1107.

Gold R, Giovannoni G, Phillips J T, Fox R J, Zhang A, Meltzer L, Kurukulasuriya N C "Efficacy and safety of delayed-release dimethyl fumarate in patients newly diagnosed with relapsing-remitting multiple sclerosis (RRMS)." Multiple Sclerosis Journal (2015) 21(1):57-66. doi:10.1177/1352458514537013.

Harris J M and Chess R B "Effect of pegylation on pharmaceuticals." Nature reviews. Drug discovery (2003) 2(3):214-221. doi:10.1038/nrd1033

Knop K, Hoogenboom R, Fischer D and Schubert U "Poly (ethylene glycol) in Drug Delivery: Pros and Cons as Well as Potential Alternatives." Angew. Chemie Int. Ed., (2010) 49(36):6288-6308. doi:10.1002/anie.200902672.

Linker R A, Lee D H, Ryan S, van Dam A M, Conrad R, Bista P, Zeng W, Hronowsky X, Buko A, Chollate S, Ellrichmann G, Bruck W, Dawson K, Goelz S, Wiese S, Scannevin R H, Lukashev M, Gold R. "Fumaric acid esters exert neuroprotective effects in neuroinflammation via activation of the Nrf2 antioxidant pathway," Brain (2011) 134(3), 678-692. doi:10.1093/brain/awq386.

Litjens N H, Burggraaf J, van Strijen E, van Gulpen C, Mattie H, Schoemaker R C, van Dissel J T, Thio H B, Nibbering P H. "Pharmacokinetics of oral fumarates in healthy subjects." British J Clinical Pharmacology (2004) 58(4):429-32. doi:10.1111/j.1365-2125.2004.02145.x.

Ockenfels H M, Schultewolter T, Ockenfels G, Funk R, Goos M. "The antipsoriatic agent dimethylfumarate immunomodulates T-cell cytokine secretion and inhibits cytokines of the psoriatic cytokine network." British Journal of Dermatology (1998) 139(3):390-395. doi: 10.1046/j.1365-2133.1998.02400.x.

Paraiso H C, Kuo P C, Curfman E T, Moon H J, Sweazey R D, Yen J H, Chang F L, Yu I C "Dimethyl fumarate attenuates reactive microglia and long-term memory deficits following systemic immune challenge." J Neuroinflammation. (2018) 15(1):100. doi:10.1186/s12974-018-1125-5.

Parodi B, Rossi S, Morando S, Cordano C, Bragoni A, Motta C, Usai C, Wipke B T, Scannevin R H, Mancardi G L, Centonze D, Kerlero de Rosbo N, Uccelli A. "Fumarates modulate microglia activation through a novel HCAR2 signaling pathway and rescue synaptic dysregulation in inflamed CNS," Acta Neuropathol. (2015) 130(2): 279-95. doi:10.1007/s00401-015-1422-3.

Scannevin R H, Chollate S, Jung M Y, Shackett M, Patel H, Bista P, Zeng W, Ryan S, Yamamoto M, Lukashev M, Rhodes K J. "Fumarates Promote Cytoprotection of Central Nervous System Cells against Oxidative Stress via the Nuclear Factor (Erythroid-Derived 2)-Like 2 Pathway" J. Pharmacol. Exper. Therap. (2012) 341(1):274-284. doi: 10.1124/jpet.111.190132.

Seidel P, Merfort I, Hughes J M, Oliver B G, Tamm M, Roth M. "Dimethylfumarate inhibits NF-{kappa}B function at multiple levels to limit airway smooth muscle cell cytokine secretion." Am J Physiol Lung Cell Mol Physiol. (2009) 297(2):L326-39. doi:10.1152/ajplung.90624.2008.

Sheikh S I, Nestorov I, Russell H, O'Gorman J, Huang R, Milne G L, Scannevin R H, Novas M, Dawson K T. "Tolerability and Pharmacokinetics of Delayed-Release Dimethyl Fumarate Administered With and Without Aspirin in Healthy Volunteers." Clinical Therapeutics (2013) 35(10):1582-1594.e9. doi:10.1016/j.clinthera.2013. 08.009.

Strassburger-Krogias K, Ellrichmann G, Krogias C, Altmeyer P, Chan A, Gold R "Fumarate treatment in progressive forms of multiple sclerosis: first results of a single-center observational study." Ther Adv Neurol Disord. (2014) 7(5):232-8. doi:10.1177/1756285614544466.

Tecfidera FDA Approved Label (12/2017), available at https://www.accessdata.fda.gov/ Veronese F M, Pasut G. "PEGylation, successful approach to drug delivery," Drug Discovery Today (2005) 10(21):1451-1458. doi:10.1016/S1359-6446(05)03575-0.

Yao Y, Miao W, Liu Z, Han W, Shi K, Shen Y, Li H, Liu Q1, Fu Y, Huang D, Shi F D. "Dimethyl Fumarate and Monomethyl Fumarate Promote Post-Ischemic Recovery in Mice." Transl Stroke Res. (2016) 7(6):535-547. doi:10.1007/s12975-016-0496-0

The invention claimed is:

1. An injectable dosage form comprising an injectable pharmaceutical composition comprising a compound of formula (I):

wherein R1 represents a polymeric moiety selected from the group consisting of polyethylene glycol (PEG), poly(glycolide), poly(lactic acid), poly(lactide), poly(caprolactone), poly(lactide-co-caprolactone), poly(lactide-co-glycolide), and poly(lactic acid)-butanol, wherein the composition is adapted for administration to a patient parenterally.

2. The composition of claim 1 wherein R1 represents PEG having repeating units —(CH2-CH2-O)n-, wherein n=1-455.

3. The composition of claim 2 wherein the PEG moiety is PEG-400 having n=8-10.

4. The composition of claim 2 wherein the PEG moiety is PEG-1000 having n=21-25.

5. The composition of claim 2 wherein the PEG moiety is PEG-2000 having n=43-48.

6. The composition of claim of 2 wherein the PEG moiety is PEG-3000 having n=65-71.

7. The composition of claim 2 wherein the PEG moiety is PEG-5000, having n=112-117.

8. The composition of claim 2 wherein the PEG moiety has a molecular weight of approximately between 950 and 1050.

9. The composition of claim 2 wherein the compound of formula (I) has the 400 MHz proton NMR spectrum of FIG. 2A.

10. The composition of claim 2 wherein the compound of formula (I) has the 400 MHz proton NMR spectrum of FIG. 2B.

11. The composition of claim 2 wherein the compound of formula (I) has the following 400 MHz proton NMR spectrum in deuterated chloroform (CDCl3):

δ 3.33 (s, 3H, OCH3 of mPEG), 3.44-3.75 (m, backbone OCH2CH2O of mPEG), 3.79 (s, 3H, OCH3 of MMF), 4.35 (m, 2H, OCH2 of mPEG adjacent to MMF), 6.87 (m, 2H, —CH=CH— of MMF).

12. The composition of claim 2 wherein the compound of formula (I) has the following 400 MHz proton NMR spectrum in deuterated chloroform (CDCl3):

δ 6.87 (s, 2H, —CH=CH— of MMF), 4.35 (m, 2H, OCH2 of mPEG adjacent to MMF), 3.81 (s, 3H, OCH3 of MMF) 3.43-3.76 (m, backbone OCH2CH2O of mPEG), 3.36 (s, 3H, OCH3 of PEG).

13. The composition of claim 2 wherein the compound of formula (I) has a molecular weight of 2192.8 g/mol.

14. The composition of claim 1 wherein the polymeric moiety comprises a straight chain.

15. The composition of claim 1 wherein the polymeric moiety comprises a branched chain.

16. The composition of claim 1 wherein the polymeric moiety comprises a substituted chain.

17. The composition of claim 1 wherein the polymeric moiety comprises an unsubstituted chain.

18. The composition of claim 1 wherein the polymeric moiety is globular.

19. A method for treating relapsing-remitting multiple sclerosis or psoriasis comprising administering to a patient parenterally an injectable pharmaceutical composition comprising a compound of formula (I)

wherein R1 represents a polymeric moiety selected from the group consisting of polyethylene glycol (PEG), poly(glycolide), poly(lactic acid), poly(lactide), poly(caprolactone), poly(lactide-co-caprolactone), poly(lactide-co-glycolide), and poly(lactic acid)-butanol.

20. The method of claim 19, wherein the polymeric moiety is polyethylene glycol (PEG).

* * * * *